US011259959B1

(12) United States Patent  
DeWoolfson et al.

(10) Patent No.: US 11,259,959 B1  
(45) Date of Patent: Mar. 1, 2022

(54) DEVICES AND METHODS FOR CORNEA TREATMENT

(71) Applicant: D&D Biopharmaceuticals, Inc., Vienna, VA (US)

(72) Inventors: Bruce H. DeWoolfson, Vienna, VA (US); Dale P. DeVore, Chelmsford, MA (US); Michael Luttrell, Dayton, OH (US)

(73) Assignee: D&D Biopharmaceuticals, Inc., Vienna, VA (US)

( * ) Notice: Subject to any disclaimer, the term of this patent is extended or adjusted under 35 U.S.C. 154(b) by 0 days.

(21) Appl. No.: 17/133,023

(22) Filed: Dec. 23, 2020

Related U.S. Application Data (60) Provisional application No. 63/109,029, filed on Nov. 3, 2020.

(51) Int. Cl.
| | |
|---|---|
| *A61F 9/00* | (2006.01) |
| *A61M 5/19* | (2006.01) |
| *A61M 5/32* | (2006.01) |
| *A61M 39/24* | (2006.01) |
| *A61K 31/351* | (2006.01) |
| *A61K 47/24* | (2006.01) |

(52) U.S. Cl.  
CPC .......... *A61F 9/0017* (2013.01); *A61K 31/351* (2013.01); *A61K 47/24* (2013.01); *A61M 5/19* (2013.01); *A61M 5/3202* (2013.01); *A61M 39/24* (2013.01); *A61M 2202/04* (2013.01); *A61M 2202/064* (2013.01); *A61M 2205/3324* (2013.01); *A61M 2205/584* (2013.01); *A61M 2210/0612* (2013.01)

(58) Field of Classification Search  
CPC ............ A61M 5/19; A61M 2205/3324; A61M 5/178; A61F 9/0026  
See application file for complete search history.

(56) References Cited

U.S. PATENT DOCUMENTS

| | | | |
|---|---|---|---|
| 4,713,446 A | 12/1987 | DeVore et al. | |
| 4,851,513 A | 7/1989 | DeVore et al. | |
| 4,898,588 A * | 2/1990 | Roberts ............... | A61M 3/0287 604/187 |
| 4,969,912 A | 11/1990 | Kelman et al. | |
| 5,067,961 A | 11/1991 | Kelman et al. | |
| 5,219,895 A | 6/1993 | Kelman et al. | |
| 5,290,228 A * | 3/1994 | Uemura ................. | A61M 5/19 604/220 |
| 5,332,802 A | 7/1994 | Kelman et al. | |

(Continued)

FOREIGN PATENT DOCUMENTS

| | | |
|---|---|---|
| WO | WO 00/35427 | 6/2000 |
| WO | WO 2009/120549 A2 | 10/2009 |

*Primary Examiner* — Catharine L Anderson  
*Assistant Examiner* — Arjuna P Chatrathi  
(74) *Attorney, Agent, or Firm* — Bookoff McAndrews, PLLC (57) ABSTRACT

Medical devices and methods of treating subjects using such medical devices are described. The medical device may include a housing with at least two chambers including a first chamber adjacent to a second chamber; a barrier between the first chamber and the second chamber; and a soft, flexible base. The first and second chambers may be airtight, the barrier configured to establish fluid communication between the first chamber and the second chamber upon an application of force to the barrier.

18 Claims, 5 Drawing Sheets

(56) References Cited

U.S. PATENT DOCUMENTS

| | | |
|---|---|---|
| 5,476,515 A | 12/1995 | Kelman et al. |
| 5,480,427 A | 1/1996 | Kelman et al. |
| 5,631,243 A | 5/1997 | Kelman et al. |
| 5,951,565 A | 9/1999 | Freeman |
| 6,161,544 A | 12/2000 | DeVore et al. |
| 6,183,498 B1 | 2/2001 | DeVore et al. |
| 6,299,856 B1 | 10/2001 | DeVore et al. |
| 6,743,435 B2 | 6/2004 | DeVore et al. |
| 6,946,440 B1 | 9/2005 | DeWoolfson et al. |
| 7,402,562 B2 | 7/2008 | DeWoolfson et al. |
| 7,824,372 B1 * | 11/2010 | Kurup ............... A61F 9/0017 604/116 |
| 8,221,353 B2 * | 7/2012 | Cormier ............ A61F 9/0017 604/117 |
| 8,672,904 B1 * | 3/2014 | Schultz ............. A61M 3/0262 604/302 |
| 9,198,673 B2 * | 12/2015 | Stone ............... A61B 17/1635 |
| 9,399,102 B2 | 7/2016 | DeWoolfson et al. |
| 10,342,697 B2 * | 7/2019 | Friedman ......... A61K 31/525 |
| 2003/0060763 A1 * | 3/2003 | Penfold ............. A61F 9/0017 604/116 |
| 2003/0065293 A1 * | 4/2003 | Hess ................. A61F 9/0026 604/294 |
| 2005/0106270 A1 * | 5/2005 | Devore .............. A61K 33/00 424/722 |
| 2009/0105127 A1 | 4/2009 | Thompson et al. |
| 2010/0106097 A1 * | 4/2010 | Elmouelhi ....... A61M 5/14276 604/189 |
| 2011/0060267 A1 | 3/2011 | DeWoolfson et al. |
| 2011/0086802 A1 * | 4/2011 | Dewoolfson ...... A61K 31/185 514/17.2 |
| 2011/0264033 A1 * | 10/2011 | Jensen .............. G16H 20/17 604/65 |
| 2011/0282305 A1 * | 11/2011 | Weiser .............. A61M 35/003 604/298 |
| 2012/0265171 A1 * | 10/2012 | Thorne, Jr. ......... A61M 5/19 604/518 |
| 2013/0237935 A1 * | 9/2013 | Kouyoumjian ..... A61F 9/0026 604/296 |
| 2015/0057608 A1 * | 2/2015 | Hitscherich, Jr. ... A61M 5/19 604/91 |
| 2016/0000885 A1 | 1/2016 | Thompson et al. |
| 2016/0270956 A1 * | 9/2016 | Lin .................... A61F 9/0017 |

\* cited by examiner

DEVICES AND METHODS FOR CORNEA TREATMENT

CROSS-REFERENCE TO RELATED APPLICATIONS

This application claims priority to U.S. Application No. 63/109,029, filed on Nov. 3, 2020, which is incorporated by reference herein in its entirety.

TECHNICAL FIELD

The present disclosure is directed to devices for delivering compositions to an eye of a subject, e.g., in preparation for, during, and/or after a medical procedure. The devices herein may facilitate mixing and delivering one or more agents such as, e.g., an acylating agent, to the eye, including the corneal epithelium. The device may include a base configured to contact part of the eye (e.g., the surface of the eye), and a display such as an indicator to provide information related to the composition. For example, the device may allow for mixing the acylating agent with a liquid to form a composition in the form of a solution, and the indicator may indicate the pH or pH range of the composition after mixing.

BACKGROUND

The corneal epithelium is the outermost tissue layer of the cornea and serves to protect the eye from intrusions of foreign substances into the underlying tissue structures. The epithelium is four to five cell layers in thickness and the junctures between the cells in each layer are tightly connected. The tight protective shield of the epithelium makes it difficult to introduce desired agents into the cornea, such as antibiotics to fight an infection, dilating agents to open the pupil to permit examination of the retina, or other therapeutic or pharmaceutical agents.

The treatment of many ophthalmic diseases and post-operative conditions require frequent administration of drugs to the ocular tissues. Many medications must be applied topically to the eye, and one common form of treatment is the use of drops or ointments. The topical formulation is administered by the patient or caregiver using an eye dropper or dispenser. However, a substantial disadvantage of this method of drug delivery is that the medication can rapidly drain from the ocular surface into the lacrimal system through an opening in the eyelid called the punctum. Furthermore, the medication can be rapidly diluted by tears secreted by the lacrimal gland. Another approach for localized drug delivery involves the injection of the drug directly under the conjunctiva or Tenon capsule, intracamerally or intra-vitreally. This approach can require periodic injections of the drug to maintain an effective concentration at the target site and has many potential adverse effects. Current treatment methods like these can result in sporadic delivery of medication with unpredictable dosage at the target tissue. Intermittent administration can also lead to an initial overdosage with a rapid decrease in concentration to ineffective levels, due to dilution and lacrimal drainage.

SUMMARY

The present disclosure describes devices for preparing and delivering therapeutic agents to the eye. For example, the devices herein allow for mixing and controlled delivery of compositions which temporarily open up the tight junctures of the epithelial cells. Such compositions therefore create channels through which therapeutic and/or pharmaceutical agents, or other suitable medical compositions, can be introduced into the eye. The devices herein facilitate administration of a composition with the desired, appropriate characteristics, such as pH value, to a subject without resorting to use of multiple implements and/or without specialized skill in mixing and delivering the composition within the desired, often limited, timeframe for efficacy.

The present disclosure includes, for example, a medical device comprising a housing comprising at least two chambers including a first chamber and a second chamber; a barrier between the first chamber and the second chamber; a shaft slidable within the housing, along a longitudinal axis of the device, towards the at least two chambers; and a soft, flexible base configured for direct application to an eye of a subject; wherein the barrier is configured to establish fluid communication between the first chamber and the second chamber upon an application of force to the barrier. The barrier may be or include a one-way valve, for example. The base is optionally detachable from the housing. The device may further comprise a cap coupled to, and detachable from, the housing. Optionally, the cap includes a stopper configured to cover an outlet of the housing. According to some aspects, the device also comprises at least one indicator coupled to an inner surface of at least one of the first chamber or the second chamber. For example, the indicator(s) may be or include a visual indicator configured to exhibit a change in color in the presence of a change in pH. The first chamber may be distal to the second chamber and/or a distal end of the first chamber may be adjacent to the base. The distal end of the first chamber may be formed by a cap coupled to, and detachable from, the base, for example. The first chamber may be open to atmosphere upon removing the cap from the base. As mentioned above, the cap may include a stopper.

According to some aspects of the present disclosure, the device further comprises a first agent (or first component of a composition) contained in the first chamber and a second agent (or second component of the composition) contained in the second chamber. In at least one example, the first agent is in powder form, and the second agent is in liquid form. For example, the first agent may comprise an acylating agent and/or the second agent may comprise an activator, e.g., an activator liquid.

The present disclosure also includes a medical device comprising a housing comprising a first chamber and a second chamber, wherein the first chamber contains a first agent (or first component of a composition) and the second chamber contains a second agent (or second component of the composition) different from the first agent; a one-way valve between the first chamber and the second chamber; and a soft, flexible base configured for direct application to an eye of a subject; wherein the valve is configured to establish fluid communication between the first chamber and the second chamber upon an application of force to the valve. Such devices may further comprise a shaft slidable within the housing, along a longitudinal axis of the device, towards the first chamber and the second chamber. In at least one example, the first agent comprises an acylating agent, and the second agent comprises a buffer solution. The acylating agent may comprise, e.g., an anhydride in powder form.

The present disclosure also includes methods of using the devices above and disclosed elsewhere herein. For example, the present disclosure includes a method of treating a subject using a device comprising a housing that includes a first chamber that contains an acylating agent, a second chamber that contains an activator liquid, and barrier between the first chamber and the second chamber, wherein the method comprises preparing a composition by combining the acylating agent with the activator liquid by applying force to the barrier to establish fluid communication between the first and second chambers; and administering the composition to an eye of the subject. The subject may be, for example, a human subject. The device may comprise a soft, flexible base coupled to the housing, wherein administering the composition includes contacting the eye with the base. The barrier of the device may include a valve. Applying force to the barrier may include sliding a shaft within the housing to force the activator liquid through the valve. According to some examples, the composition has a pH of about 8.4 to about 8.6 when administered to the subject. Optionally, the device includes at least one indicator coupled to an inner surface of the first chamber or the second chamber, and the indicator signals when the composition reaches a pH of about 8.4 to about 8.6. The composition may be applied to the eye of the subject within a limited timeframe of combining the acylating agent with the activator liquid. For example, the composition may be applied to the eye within 30 seconds to 5 minutes of combining the acylating agent with the activator liquid, such as within 30 seconds to 2 minutes, or within 4 minutes, within 3 minutes, within 2 minutes, within 1 minute, within 45 seconds, or within 30 seconds of combining the acylating agent with the activator liquid.

BRIEF DESCRIPTION OF THE FIGURES

The accompanying figures, which are incorporated in and constitute a part of this specification, illustrate various examples and together with the description, serve to explain the principles of the present disclosure.

FIGS. 1A-1C show an exemplary medical device, in accordance with aspects of the present disclosure, wherein

DETAILED DESCRIPTION

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value. Any aspect described herein as exemplary is not to be construed as preferred or advantageous over other aspects. Rather, the term "exemplary" is used in the sense of example or illustrative. The terms "comprise," "include," "have," "with," and any variations thereof are used synonymously to denote or describe non-exclusive inclusion.

The devices and methods herein may facilitate preparing and administering compositions to the eye, including compositions prepared from multiple components. For example, the compositions herein may be formulated to be applied immediately or shortly after preparation, that is, after mixing two or more components together. The timeframe between mixing components and administering the composition to a subject may be a consideration where parameters such as pH, viscosity, temperature, etc., may change over time. The devices herein may include chambers configured to keep components separate until such time as a user engages and operates the device to mix the components for subsequent application to a subject. The device may include, for example, at least two chambers, wherein each chamber contains a component to be mixed together when initiated by a user via operation of the device.

While the following describes an exemplary composition prepared via an acylation reaction to illustrate aspects of the devices and methods herein, the present disclosure is not limited to such compositions. Rather, the devices herein may be used to prepare other compositions from two or more components, including compositions formulated for administration to a subject and having properties that change over time (e.g., pH, viscosity, temperature, etc.).

Some examples of the present disclosure may be used to deliver compositions to the eye to permit trans-corneal penetration of pharmaceutical agents and other therapeutic agents. Such compositions may be prepared by combining an acylating agent with an activator liquid. In the case of epithelial tight junctures, the acylation reaction is understood to open the junctures between epithelial cells. These junctures provide open channels allowing diffusion of active agents into and through the corneal stroma and into sub-corneal tissues.

For example, the acylating agent may comprise an anhydride, an acid chloride, a sulfonyl chloride, or sulfonic acid. Suitable anhydrides include agents that change the net charge from positive to negative. Exemplary anhydrides suitable for the devices and methods herein include, but are not limited to, maleic anhydride, succinic anhydride, glutaric anhydride, citractonic anhydride, methyl succinic anhydride, itaconic anhydride, methyl glutaric anhydride, dimethyl glutaric anhydride, phthalic anhydride, acetic anhydride, chloroacetic anhydride, propionic anhydride, butyric anhydride, isobutyric anhydride, isovaleric anhydride, and hexanoic anhydride. Anhydrides are sensitive to conversion to the corresponding acid (e.g., conversion of glutaric anhydride to glutaric acid) when exposed to and/or mixed with an aqueous solution. Such anhydrides are also reactive with deprotonated amines on protein molecules. Amine groups on protein molecules can be deprotonated by exposure to an alkaline buffer, for example. Exemplary acid chlorides suitable for the devices and methods herein include, but are not limited to, oxalyl chloride, malonyl chloride, acetyl chloride, propionyl chloride, dichloropropionyl chloride, butyryl chloride, isobutyryl chloride, and valeryl chloride. Exemplary sulfonyl chlorides suitable for the devices and methods herein include, but are not limited to, chlorosulfonylacetyl chloride, chlorosulfonylbenzoic acid, 4-chloro-3-(chlorosulfonyl)-5-nitroebnzoic acid, 3-(chlorosulfonyl)-P-anisic acid, ethane sulfonyl chloride, methane sulfonyl chloride, and 1-butane sulfonyl chloride.

Acylation reagents may preferentially react with protein groups, such as lysine groups, that have been deprotonated. These same reagents also have the potential to react with N-terminal amino groups, with tyrosyl residues and cysteinyl residues. Deprotonation of ε-amino groups on lysine may be achieved by increasing the pH to alkaline levels. Effective pH levels for deprotonation of ε-amino groups on lysine is generally around pH 10.0. However, reactions with acylation agents typically occur between pH 8.0 and 9.0, and reactivity is generally slow at pH 7.0. The active acylating agent may react with deprotonated protein(s) to alter the protein solubility. Accordingly, timing is a consideration for effective delivery of acylating agents in an alkaline buffer solution to proteins that have also been exposed to and deprotonated by an alkaline buffer.

Acylation reaction kinetics may depend on (1) reaction pH (e.g., reactions may occur faster at higher pH, such as up to pH 10.0), (2) the concentration of acylation agent, and/or (3) hydrolysis of the acylation agent to an inactive acid in aqueous solution (time factor). As discussed above, reactivity is greater at higher pH. When proteins are acylated in solution, the pH is understood to constantly adjust to alkaline pH, for example pH 9.0. The effectiveness of acylation also may depend on the concentration of the active acylation agent. The acylation agent may rapidly hydrolyze into an inactive acid with a concurrent reduction in pH. The acidic form may be inactive, such that as the pH drops, the rate of acylation also drops due to less reactive acylation agent available and lower pH that does not favor reactivity.

The reaction involves a balance between pH and the concentration of active acylation agent. In the case of an anhydride, for example, the ratio of inactive acylation agent (e.g., in acidic form) and active acylation agent (e.g., in anhydride form) changes as soon as the anhydride form is mixed with aqueous solution. The time for complete hydrolysis of anhydride to acid is relatively short, e.g., less than 1 minute. During this time, the pH drops making the active form less reactive. Therefore, both reaction pH and the concentration of active acylation agent are variables to be controlled for effective treatment.

The devices described in this application provide for effective and controlled delivery of pH-sensitive agents to a subject. For example, the devices and methods herein may be useful for creating create trans-epithelial channels for effective delivery of desired ocular therapeutic agents.

According to some examples herein, a composition formulated for administration to the eye is produced by mixing two components each contained in a respective chamber: (1) an acylating agent (e.g., a powdered anhydride) enclosed in an airtight chamber before use, so that moisture from the air will not degrade the properties of the powder before mixing, and (2) an activator (e.g., an activator liquid) enclosed in a separate airtight chamber before use. Exemplary activator liquids include alkaline buffer solutions such as phosphate, e.g., monobasic sodium phosphate, disodium hydrogen phosphate and/or potassium dihydrogen phosphate, and other alkaline pH buffer solutions such as a carbonate buffer. The activator may have a pH ranging from about 7.5 to about 9.5, e.g., about 8.0 to about 9.0, or about 8.2 to about 8.5.

To prepare the composition, the acylating agent (e.g., in powder form) and the activator (e.g., in liquid form) may be mixed together by placing the two chambers in fluid communication with each other, such as by breaking a membrane or otherwise opening a barrier between the two chambers containing the respective components. In at least one example, the device includes a one-way valve between chambers, such as a duckbill valve to allow flow in one direction while preventing flow in the opposite direction. Such a valve may serve as a barrier between chambers.

The devices herein may ensure that the components (e.g., acylating agent powder and activator liquid) are thoroughly mixed together prior to administration to a subject. For example, a user may agitate the device, such as by shaking, to break the membrane and mix components. Additionally or alternatively, the device may include a mechanism that can be engaged by a user to establish fluid communication between chambers. For example, in the case of a one-way valve, the user may cause one component (e.g., a liquid) to move (e.g., flow) from one chamber, through the valve to mix with a second component (e.g., a powder) in the other chamber. The components may be combined, for example, by forcing one of the components through the valve, optionally including by breaking a membrane covering the exit of the valve. Optionally, the user may shake or otherwise agitate the device to mix the components once combined into a single chamber. After the components (e.g., powder and liquid) are mixed together, the resulting composition may have a basic pH that begins to drop over time. For proper efficacy, it may be desirable to administer the composition within a given timeframe, e.g., such that the composition is administered to the corneal epithelium when the pH has reached the desired level. For example, the composition may be suitable for administration at a pH ranging from about 8.3 to about 8.7, such as about 8.4 to about 8.6, or about 8.5.

In order for the administering clinician or other medical professional to know when the desired pH has been reached, the device may provide audio and/or visual indicators signaling that the composition is ready to be applied to the eye. In at least one example, the device includes a visual indicator in the form of a strip configured to exhibit a specified color and/or to change color when the desired pH has been reached. For example, one or both chambers of the device may include a strip coupled to the inner wall surface in a suitable location so as to contact the composition formed upon mixing of the components.

The device also may include features to ensure that after applying the composition to the eye, the composition is held in place on the surface of the cornea for a sufficient amount of time. For example, the composition may be kept in contact with the cornea for at least 15 seconds or at least 30 seconds, such as about 15-60 seconds, or about 30-45 seconds. Such features of the device may include a soft and flexible base at or proximate a distal end of the device, to serve as a dam to hold the composition in place. The base may be permanently affixed to the device or may be detachable, e.g., configured to attach to an end of the device by suitable mating elements or features (e.g., friction fit, snap fit, clips, threaded portions, Luer lock connectors, tabs, etc.).

Further, the device may include a detachable cap to keep the device airtight, liquid tight, and/or sterile before administering the composition. The cap may serve as a temporary stopper to the outlet of the device, e.g., to prevent the composition and/or individual components thereof from leaking. For example, the cap may be maintained in place while mixing of components and removed before administering the composition to the eye. Removing the cap may uncover the outlet to allow for injection of the composition onto the cornea. The cap may include features such as a Luer lock connector or other fluid-tight connectors for releasing the cap from the device.

Figure 1A:
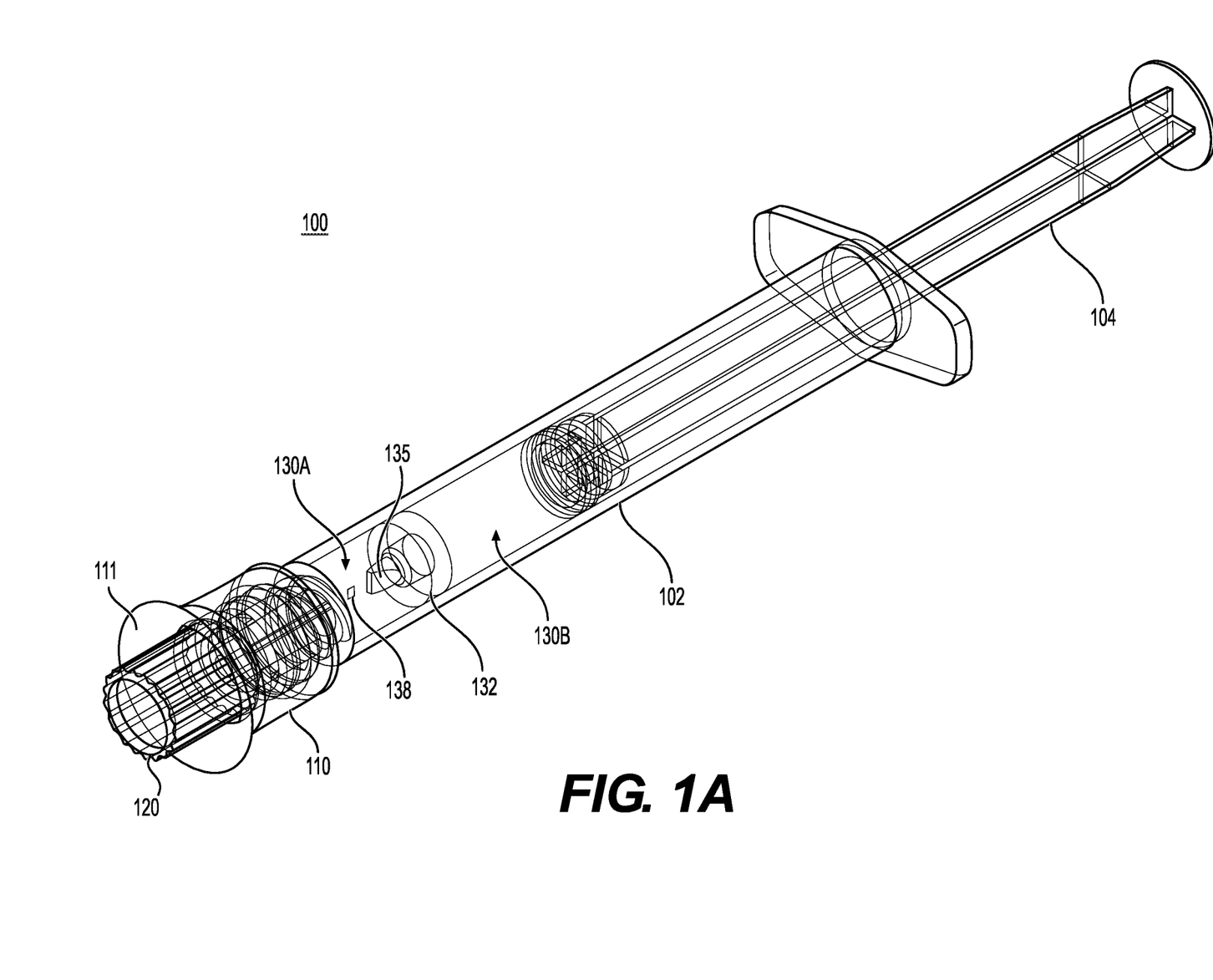
FIG. 1A shows a perspective view.
Figure 1B:
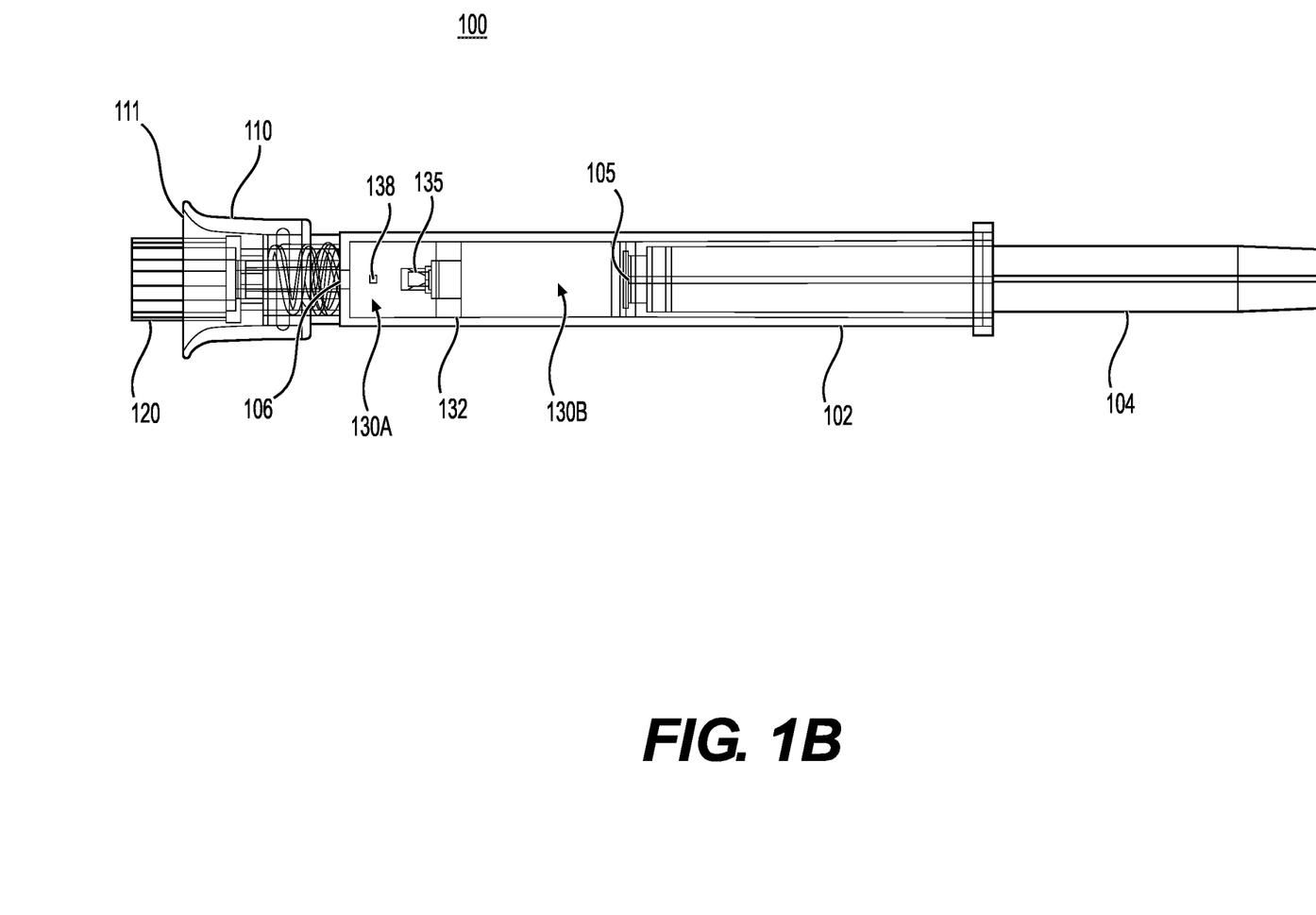
FIG. 1B shows a side view.
Figure 1C:
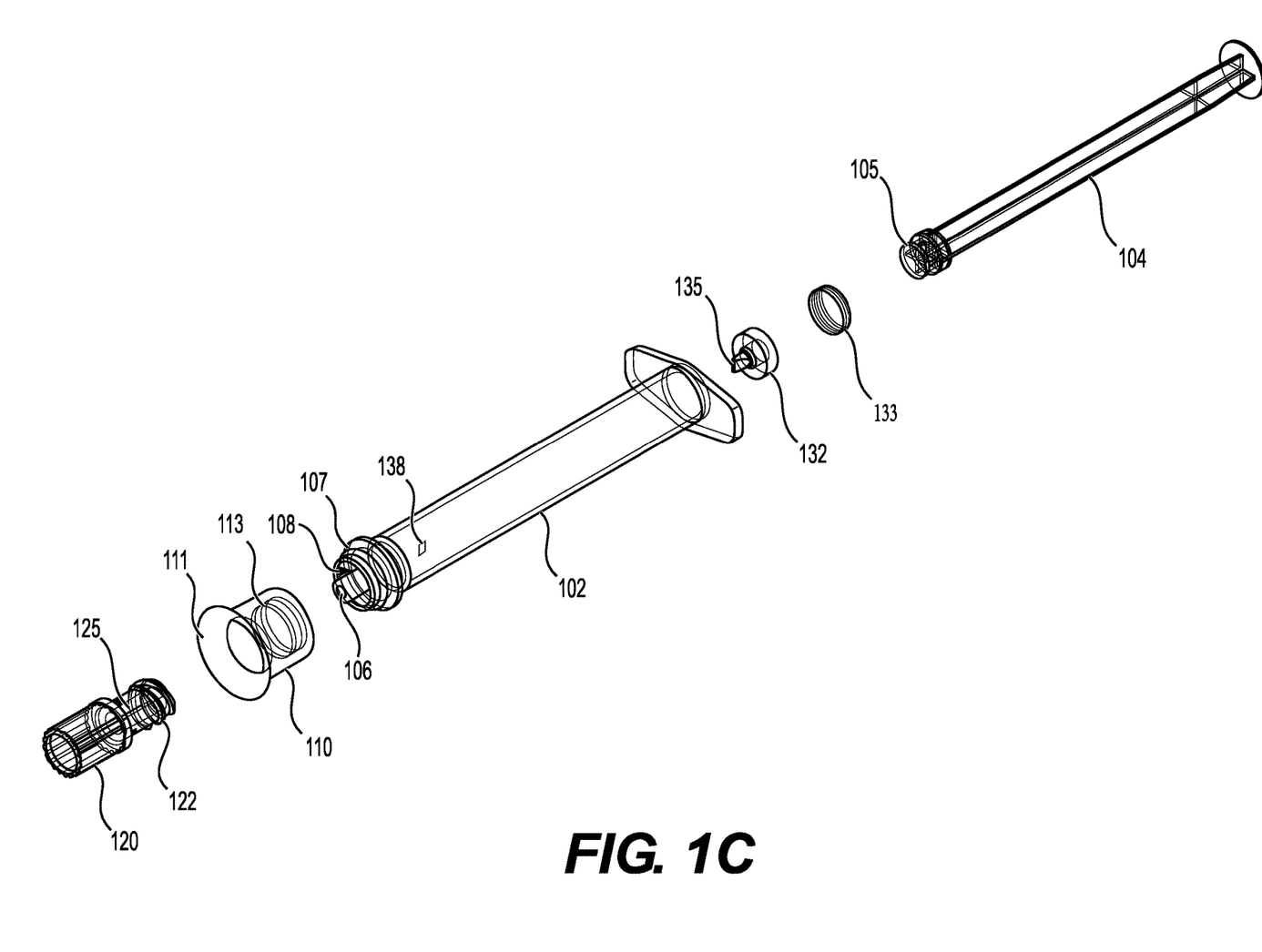
FIG. 1C shows an exploded view.

FIGS. 1A-1C illustrate an exemplary medical device 100 according to some examples herein. It is understood that the devices herein may include additional or fewer features than those illustrated in the figures, in accordance with the disclosure herein and variations included herein. The device 100 may be configured to be handheld (e.g., by a single user) during mixing of the composition and administration to the eye. The device 100 resembles a syringe in the example illustrated, although other shapes and configurations can be used.

As shown, the medical device 100 comprises a housing 102 that includes two chambers 130A and 130B separated by a barrier in the form of a valve 132. The device 100 also includes a shaft in the form of a plunger 104 that is slidable within the housing 102. Chamber 130A extends between the distal end of the housing 102 and the valve 132, and chamber 130B extends between the valve 132 and the distal end 105 of the plunger 104. A sealing element 133 such as a molded plunger or O-ring provides a seal between the distal end 105 of the plunger 104 and the inner surface of the housing 102. The plunger 104 may be moved distally such that the distal end 105 of the plunger 104 moves towards the valve 132, thereby decreasing the volume of chamber 130B. Moving the plunger distally may force a material contained within chamber 130B to pass through the valve 132 and enter chamber 130A. The chambers 130A, 130B may have the same dimensions or different dimensions. In some examples, each chamber 130A, 130B has a volume ranging from about 0.1 mL (0.1 cm$^3$) to about 10 mL (10 cm$^3$), such as about 0.5 mL to about 5 mL, about 1 mL to about 3 mL, about 5 mL to about 8 mL, about 0.2 mL to about 1 mL, or about 0.5 mL to about 2 mL.

The valve 132 may be a one-way valve with a closeable aperture 135, such as, e.g., a duckbill valve that includes two or more flaps. For example, the valve 132 may be positioned to provide for one-directional flow, such as from chamber 130B to chamber 130A in a proximal to distal direction. Thus, for example, chamber 130A may contain a first component of a composition, and chamber 130B may contain a second component of the composition. According to some aspects, the valve 132 may keep each chamber separated from the other, and optionally airtight and/or water tight from the other chamber. The chambers may be airtight from the surrounding environment. The first and second components may be in the same form (e.g., liquid or solid) or different forms (e.g., solid and liquid). According to some examples, chamber 130A may contain a solid (e.g., an acylating agent in solid form, such as a powder anhydride) and chamber 130B may contain a liquid (e.g., an activator liquid).

The device 100 also comprises a base 110 and a cap 120. As mentioned above, the base 110 may be permanently affixed or detachable from the housing 102. In the exemplary device 100 shown, the base 110 includes mating features 113 complementary to mating features 107 of the housing 102 to allow for attachment and detachment of the base 110 from the housing 102. The mating features 107, 113 may be, for example, complementary threads, tabs, or elements with dimensions providing for a snap-fit or other friction-fit. The distal end 111 of the base 110 has a surface configured to contact a subject's eye during administration of a composition. For example, the base 110 may comprise a biocompatible polymer such as silicone, e.g., low durometer silicone, or other material suitable for contacting the eye. The distal end 111 may be at least partially flexible and/or soft, or otherwise configured to conform to different dimensions and/or curvatures of the eye. As shown in FIG. 10, the base 110 has a generally cylindrical shape with a lumen therethrough, wherein the distal end 111 flares radially outward. The distal end 111 may be soft and flexible to accommodate the convex curvature of the eye.

The cap 120 may have mating features complementary to the housing 102 in order to seal and unseal the outlet 106 of the device 100, the outlet being in fluid communication with chamber 130A. For example, the cap 120 may include mating features 122 (e.g., a male Luer lock connector) complementary to mating features 108 (e.g., a female Luer lock connector) of the housing 102. Mating features other than Luer lock connectors may be used including, e.g., threads, tabs, friction fit, etc. When coupled to the housing 102, the cap 120 may provide a fluid-tight connection to prevent material(s) within the housing 102 from leaking. The cap 120 may include a stopper 125 that aligns with the outlet 106 when coupled to the housing 102, wherein the stopper 125 may be an integral part of the cap 120 or may be a separate component coupled to an inner surface of the cap 120. For example, the stopper 125 may receive or be received within the outlet 106 to cover the outlet 106. As shown in FIG. 10, the outlet 106 may be at a distalmost end of the housing 102, wherein the outlet 106 is distal to the mating features 107, 108. Thus, for example, the outlet 106 may partially extend into the base 110 (see FIG. 1B). In some examples, the cap 120 may have mating features complementary to the base 110 to directly couple the cap 120 to the base 110. Alternatively, the cap 120 may extend through the lumen of the base 110 to attach to the housing 102 without connecting to the base 110.

In view of the above discussion, it will be appreciated that the housing 102 may include two sets of mating features, e.g., first mating features 107 complementary to the base 110, and second mating features complementary to the cap 120. The two sets of mating features may be similar or the same types of features, or may be different from each other. When the base 110 is permanently attached or an integral part of the housing 102, the housing 102 may include only mating features complementary to the cap 120.

Figure 2:
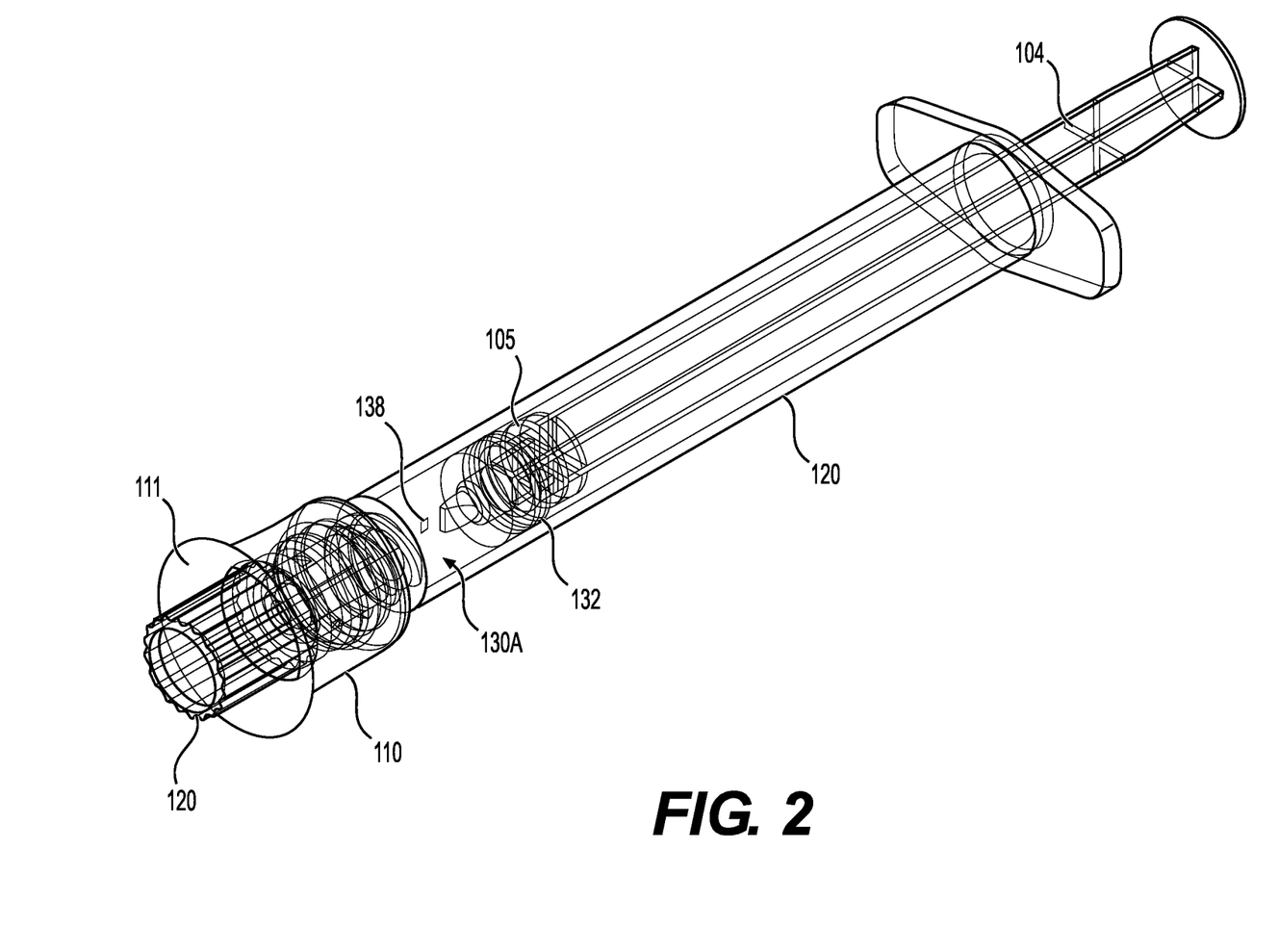
FIGS. 2 and 3 illustrate different configurations of the medical device of FIGS. 1A-1C, according to some aspects of the present disclosure.
Figure 3:
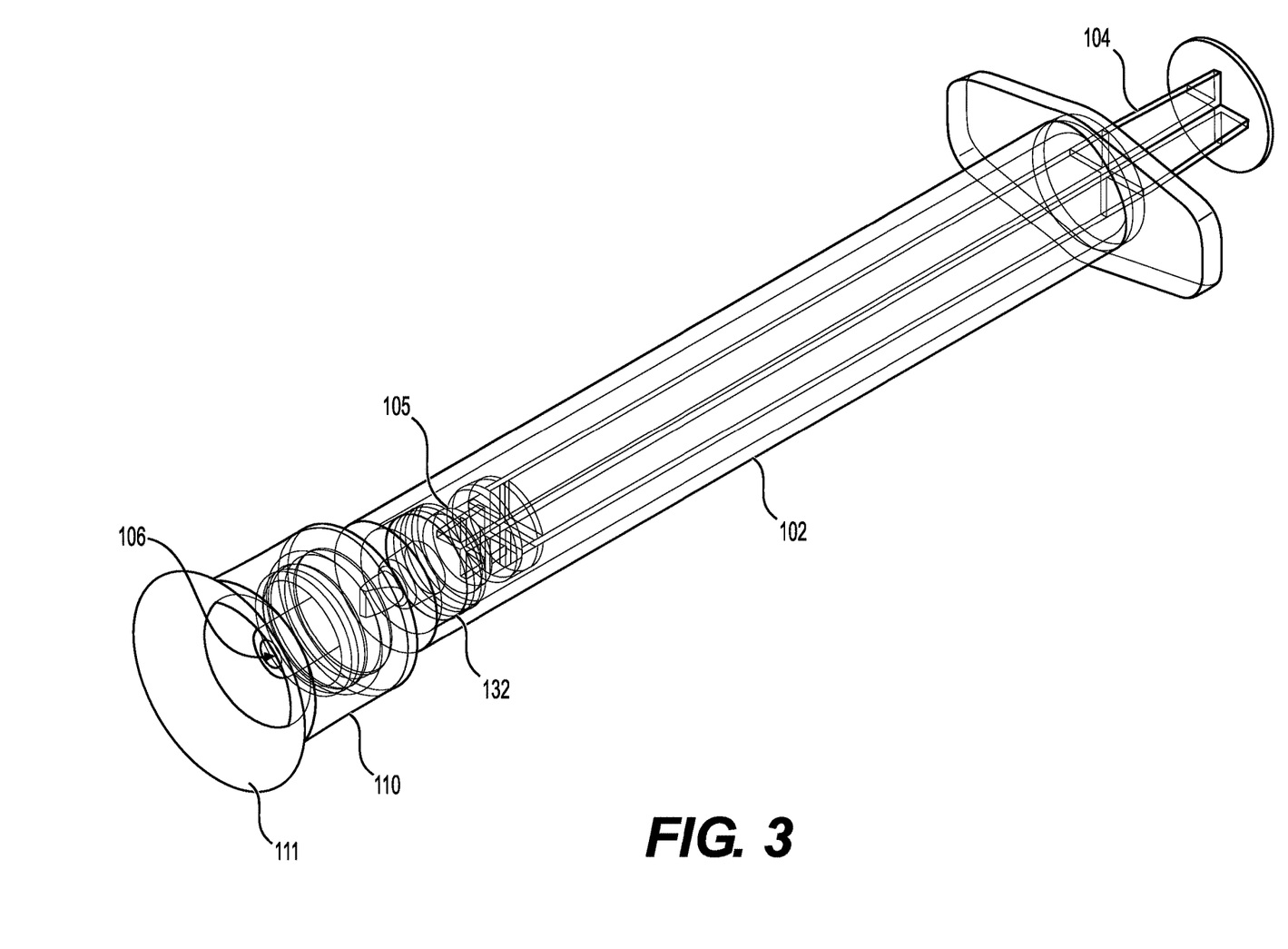

FIGS. 1A-1C illustrate a ready-to-use configuration of the device 100. For example, the device 100 may be pre-loaded with different agents in chambers 130A and 130B, wherein chamber 130A includes an indicator 138, prior to use. FIGS. 2 and 3 show different configurations of the device 100 during use. For example, components of a composition may be combined by introducing a first component (e.g., a liquid) from chamber 130B into chamber 130A, e.g., by advancing the plunger 104 of the device 100 towards chamber 130B to open the valve 132 by forcing the first component through the aperture 135 of the valve 132 to mix with a second component (e.g., a powder) of the composition in chamber 130A, without moving valve 132. This is illustrated by the sequence from the configuration shown in FIG. 1A to the configuration shown in FIG. 2. Once the distal end 105 of the plunger 104 is advanced so as to contact or otherwise be adjacent to the proximal side of the valve 132, as shown in FIG. 2, chamber 130A contains both the first and second components of the composition. Optionally, the user may agitate the contents of chamber 130A, such as by gently shaking and/or inverting the device 100, to promote mixing of the components and provide sufficient mixing of the composition. The cap 120 may prevent the components from leaking outside the device 100 via the outlet 106 as they are being combined and mixed to form the composition.

As shown, chamber 130A that receives the mixed components contains an indicator 138. According to some examples herein, the indicator 138 may be a visual indicator. For example, the indicator 138 may be in the form of a strip on an inner surface of the housing 102 and configured to exhibit a specified color or change in color when the desired pH of the composition has been reached. For example, initial mixing of the two components may provide a composition with an initial pH of about 0.9. This indicator 138 may show a first color at this initial pH. Over time, such as within the first several seconds to a minute, the pH may drop. This decrease in pH may be apparent by a change in color of the indicator 138. When the pH is between about 8.4 and about 8.6, the indicator 138 may have a color that indicates to the user that the composition is ready for application to the subject's eye. Should the pH drop below the desired range, the indicator 138 again may change color to signal to the user that the composition is not appropriate for administration to the subject. A user may consult a color chart to determine the pH or approximate pH range of the composition. For example, the indicator 138 may initially appear beige and change to blue in the presence of alkaline pH around 9.0 or greater. As the pH decreases, the indicator 138 may change from blue to green, e.g., for a pH of around 8.0 to 9.0, e.g., about 8.2 to 8.7 or about 8.4 to 8.6. Further decrease in pH may cause the indicator 138 to change from green to green/yellow or yellow, e.g., for a pH below 8.0. These colors are exemplary only; it is understood that visual indicators 138 herein may be configured to exhibit other colors for particular pH values or pH ranges.

In other examples, the indicator 138 may be in the form of a light, such as an LED light. The light may change or illuminate when the target pH level has been reached. For example, the device 100 may be configured to show a green light when the target pH level has been reached (e.g., pH between about 8.4 and about 8.6). Additionally or alternatively, the indicator 138 may include an audio indicator configured to sound a chime or buzzer, for example, when the desired pH has been reached (e.g., between about 8.4 and about 8.6). It is understood that the devices herein may include a combination of indicators.

Further referring to FIG. 2, once the components of chamber 130A and 130B have been combined into chamber 130A to form the composition, the user may remove the cap 120, as illustrated in the sequence from FIG. 2 to FIG. 3, to uncover the outlet 106. The opening of the outlet 106 may be of suitably small dimensions such that the composition within chamber 130A does not exit the device 100 before additional force is applied by the plunger 104. For example, the composition may be in liquid form having a surface tension that prevents the composition from exiting the outlet 106 without the application of force. The user then may place the distal end 111 of the base 110 against the eye of a subject and advance the plunger 104 further distally, in turn moving the valve 132 distally, to expel the composition from the device 100 through the base 110, via the outlet 106, to contact the eye. As mentioned above, a first component or agent contained in chamber 130B may be passed through the valve 132 to enter chamber 130A without moving the valve 132. That is, the force sufficient to open the valve 132 may be less than the force necessary to displace the valve 132 within the housing 102. Once the distal end 105 of the plunger 104 is in contact with the valve 132, however, additional force may be applied to move the valve 132 distally via force applied by the distal end 105 of the plunger 104, and thereby expel the composition from the device 100.

The base 110 may provide an enclosed space between the eye and the housing 102 to maintain the composition in contact with the eye for a sufficient amount of time. For example, the composition may be held in contact with the eye via the device 100 for at least 30 seconds, such as 30-60 seconds or 30-45 seconds. Thereafter, the user may remove the device 100 from the eye and optionally flush the eye with a buffer solution.

The devices herein may be used to effectively open epithelial channels in preparation for the administration of other ophthalmic agents. For example, the present disclosure may facilitate topical administration of ophthalmic agents in a more controlled and consistent dosage. Such ophthalmic drugs include, but are not limited to, antibiotics, antifungals, anti-virals, anti-inflammatories, anti-glaucoma agents, anti-vascular endothelial growth factor (VEGF), and the like.

For example, the devices herein may be used in treatment of keratoconus, a condition wherein the cornea thins and develops a cone shape resulting in blurred vision. Keratoconus is a chronic, non-inflammatory disease of the cornea, characterized by corneal stromal thinning and progressive ectasia (distention) wherein the cornea assumes a conical shape, thus inducing irregular astigmatism, myopia and protrusion leading to mild to marked impairment of vision. Keratoconus is associated with weakening and thinning of corneal stroma due to abnormal collagen lamellae, changes in stromal organization, and inadequate collagen cross linking. While prior treatment methods often include removal of the corneal epidermis, necessitating an extended recovery time for the epithelial cell layer, the devices herein may be used in treatments that do not remove the epithelium. Accordingly, recovery time from the treatment procedure may be reduced. The devices herein facilitate controlled delivery of agents to the eye, including acylating agents, to rapidly open epithelial junctures without removing the epithelium. Opening epithelial junctures may allow rapid penetration of therapeutics into the stroma of the cornea. Thus, for example, riboflavin may be applied to the corneal stroma followed by UVA irradiation exposure to crosslink the riboflavin. Following delivery of the desired therapeutics, the subject may have reduced recovery time and more rapid regeneration of intact epithelium since the entire epithelium layer was not removed.

The following examples are intended to illustrate the present disclosure without, however, being limiting in nature. It is understood that the present disclosure encompasses additional embodiments consistent with the foregoing description and following examples.

EXAMPLES

Example 1

This example illustrates using the device 100 of FIGS. 1A-1C, 2, and 3 during a medical procedure. The device 100 is provided with about 4 mg glutaric anhydride powder in chamber 130A and about 1 mL phosphate buffer solution in chamber 130B. The chambers 130A, 130B are airtight and separated from one another. The cap 120 covers the outlet 106 of chamber 130A to prevent leakage from chamber 130A and to prevent air from entering chamber 130A. The indicator 138 of the device 100 is a visual indicator that appears beige in color.

Immediately before a medical procedure, such as treatment of keratoconus, a topical anesthetic is administered via eye drops to the eye of a subject. Once the anesthetic takes effect, a user slides the plunger 104 of the device 100 distally, which forces the buffer solution in chamber 130B through the valve 132 to combine with the powder anhydride in chamber 130A. The user advances the plunger 104 until the distal end of the plunger contacts the valve 132. The user then gently shakes the device 100 for several seconds to thoroughly mix the powder anhydride with the buffer solution.

Once the buffer is mixed with the anhydride, the indicator 138 in chamber 130A changes in color from beige to blue to indicate a basic pH of around 9.0. The user watches the indicator 138 to monitor for a further change in color from blue to green as the acylation reaction between the glutaric anhydride and buffer proceeds and the pH decreases. Within about 30 seconds from first mixing the powder anhydride with the buffer solution, the indicator 138 appears green to indicate a desired pH between 8.2 and 8.7. The user consults a color chart provided with the device 100 to confirm the target pH is reached.

Next, the user promptly removes the cap 120 from the housing 102 and places the distal end 111 of the base 110 again the subject's eye. The user slides the plunger 104 further distally, against the valve 132, which causes the valve 132 to move distally and force the composition through the outlet 106 and in contact with the subject's eye, within 30 seconds to 1 minute of first mixing the powder anhydride with the buffer solution. The base 110 forms a space that holds the composition in contact with the eye. The user keeps device in contact with the subject's eye for 30-45 seconds to allow the acylation agent of the composition to open the tight junctures of the epithelial cells of the subject's eye. The user then removes the device from the subject's eye and flushes the eye with a buffer solution. The subject is then ready for the next steps of the procedure, including the application of riboflavin followed by UVA light exposure. Once the medical procedure is completed, the subject recovers.

Example 2

The steps of Example 1 are repeated, except once the buffer is mixed with the anhydride, the user sets the device 100 down and becomes distracted for 2-5 minutes. The user then sees that the indicator 138 in chamber 130A has changed in color from the initial beige to yellow to indicate a pH below 8.0. The user consults a color chart provided with the device 100 to confirm the pH is below the target pH, and the anhydride as acylating agent is therefore determined to be inactive. The user thus discards the device 100 and retrieves a new device to prepare a new composition with a suitable pH for administration to the subject and efficacy for opening epithelial junctions of the subject.

Further aspects of the present disclosure include the following:

1. A medical device comprising: a housing comprising at least two chambers including a first chamber adjacent to a second chamber; a barrier between the first chamber and the second chamber; and a soft, flexible base configured for direct application to an eye of a subject; wherein the first and second chambers are each airtight, and the barrier configured to establish fluid communication between the first chamber and the second chamber upon an application of force to the barrier.

2. The device of aspect 1, wherein the barrier includes a one-way valve.

3. The device of aspect 1 or 2, wherein the base is detachable from the housing or permanently affixed to the housing.

4. The device of any one of aspects 1-3, further comprising a cap coupled to, and detachable from, the base, the housing, or both the base and the housing.

5. The device of any one of aspects 1-4, further comprising a shaft slidable within the housing, along a longitudinal axis of the device, towards the at least two chambers.

6. The device of aspect 5, wherein the shaft is a plunger.

7. The device of any one of aspects 1-6, further comprising at least one indicator coupled to an inner surface of at least one of the first chamber or the second chamber.

8. The device of aspect 7, wherein the at least one indicator is a visual indicator or an audio indicator.

9. The device of aspect 7 or 8, wherein the at least one indicator includes a strip configured to exhibit a change in color in the presence of a change in pH.

10. The device of any one of aspects 1-9, further comprising a first agent contained in the first chamber and a second agent contained in the second chamber.

11. The device of aspect 10, wherein the first agent is in powder form, and the second agent is in liquid form.

12. The device of aspect 10 or 11, wherein the first agent comprises an acylating agent, and the second agent comprises an activator liquid.

13. The device of any one of aspects 10-12, wherein the first agent and the second agent, when mixed, form a composition for temporarily opening up junctures of epithelial cells of the eye.

14. The device of any one of aspects 1-13, wherein the first chamber is distal to the second chamber, and a distal end of the first chamber is adjacent to the base.

15. The device of any one of aspects 1-14, wherein the distal end of the first chamber is formed by a cap coupled to, and detachable from, the base, the first chamber being open to atmosphere upon removing the cap from the base.

16. A method of treating a subject comprising administering a composition to an eye of the subject with the device of any one of aspects 1-15.

17. The method of aspect 17, wherein the method includes forming the composition by combining a first agent contained within the first chamber with a second agent contained within the second chamber by applying force to the barrier between the first and second chambers to establish fluid communication between the first and second chambers.

18. The method of aspect 16 or 17, wherein administering the composition includes applying the base directly to a surface of the eye for at least 30 seconds.

19. The method of aspect 17 or 18, wherein applying force to the barrier includes sliding a shaft within the housing to force the second agent against the barrier.

20. The method of any one of aspects 17-19, wherein combining the first agent with the second agent includes passing the second agent through a valve between the first chamber and the second chamber.

21. The method of aspect 20, wherein the valve is a one-way valve.

22. The method of any one of aspects 16-21, wherein the composition has a pH of about 8.4 to about 8.6 when administered to the subject.

23. The method of any one of aspects 16-22, wherein the device includes at least one indicator coupled to an inner surface of the first chamber or the second chamber, and the indicator signals when the composition reaches a pH of about 8.4 to about 8.6.

24. The method of aspect 23, wherein the indicator is a strip that changes color when the composition reaches a pH of about 8.4 to about 8.6.

25. The method of any one of aspects 16-24, wherein the composition is applied to the eye within 5 minutes, 4 minutes, 3 minutes, 2 minutes, or 1 minute of combining the first agent with the second agent.

26. The method of any one of aspects 16-22, wherein the composition temporarily opens junctures of epithelial cells of the eye.

Although the present disclosure includes reference to exemplary embodiments, the disclosure is not limited thereto. It is understood that a person of ordinary skill in the art will ascertain additional embodiments according to the principles described herein and without departing from the spirit and scope thereof, and can make various changes and modifications of the invention to adapt it to various usages and conditions. Those skilled in the art will recognize or be able to ascertain using no more than routine experimentation, many equivalents to the exemplary embodiments herein. Such equivalents are intended to be encompassed in the scope of the present disclosure.

What is claimed is:

1. A medical device comprising:
a housing comprising at least two chambers including a first chamber and a second chamber in communication with an outlet at a distalmost end of the housing, wherein the housing includes first mating features proximal to the outlet and second mating features radially inward of the first mating features;
a barrier between the first chamber and the second chamber;
a shaft slidable within the housing, along a longitudinal axis of the device, towards the at least two chambers;
a base coupled to the housing via the first mating elements of the housing, wherein the base has a soft, flexible distal end configured for direct application to an eye of a subject, the distal end of the base flaring radially outward to accommodate a convex curvature of the eye; and
a cap coupled to, and detachable from, the housing via the second mating features, the cap extending through a lumen of the base without connecting to the base;
wherein the barrier is configured to establish fluid communication between the first chamber and the second chamber upon an application of force to the barrier.

2. The device of claim 1, wherein the barrier includes a one-way valve.

3. The device of claim 1, wherein a proximal end of the base includes mating features complementary to the first mating features of the housing that fix the base to the housing, the base being detachable from the housing via the complementary mating features.

4. The device of claim 1, further comprising at least one indicator coupled to an inner surface of at least one of the first chamber or the second chamber.

5. The device of claim 4, wherein the at least one indicator is a visual indicator configured to exhibit a change in color in the presence of a change in pH.

6. The device of claim 1, further comprising a first agent contained in the first chamber and a second agent contained in the second chamber, wherein the first agent is in powder form, and the second agent is in liquid form.

7. The device of claim 6, wherein the first agent comprises an acylating agent, and the second agent comprises an activator liquid.

8. The device of claim 1, wherein the first chamber is distal to the second chamber, and a distal end of the first chamber is adjacent to the base.

9. The device of claim 1, wherein the distal end of the first chamber is formed by the cap, the first chamber being open to atmosphere upon removing the cap from the base.

10. A medical device comprising:
a housing comprising a first chamber and a second chamber, wherein the first chamber contains a first agent and the second chamber contains a second agent different from the first agent;
a one-way valve between the first chamber and the second chamber;
a base having a soft, flexible distal end configured for direct application to an eye of a subject, the base defining a lumen; and
a cap coupled to and detachable from the housing, wherein the housing is open to atmosphere through the lumen of the base upon removing the cap from the housing, the cap extending through the lumen of the base without connecting to the base;
wherein the valve is configured to establish fluid communication between the first chamber and the second chamber upon an application of force to the valve.

11. The device of claim 10, further comprising a shaft slidable within the housing, along a longitudinal axis of the device, towards the first chamber and the second chamber.

12. The device of claim 10, wherein the first agent comprises an acylating agent, and the second agent comprises a buffer solution.

13. The device of claim 12, wherein the acylating agent comprises an anhydride in powder form.

14. A method of treating a subject using a device comprising a housing that includes a first chamber that contains an acylating agent, a second chamber that contains an activator liquid, a barrier between the first chamber and the second chamber, a base distal to the housing, and a cap coupled to a distal end of the housing without connecting to the base, wherein the method comprises:
preparing a composition by combining the acylating agent with the activator liquid by applying force to the barrier to establish fluid communication between the first and second chambers;
removing the cap from the housing to uncover an outlet of the housing;
contacting an eye of the subject with a soft, flexible distal end of the base; and
administering the composition to a cornea of the eye of the subject by expelling the composition into an enclosed space between the housing and the eye, the enclosed space being defined by the base, and maintaining the composition in contact with the cornea.

15. The method of claim 14, wherein the barrier includes a valve, and applying force to the barrier includes sliding a shaft within the housing to force the activator liquid through the valve.

16. The method of claim 14, wherein the composition has a pH of about 8.4 to about 8.6 when administered to the subject.

17. The method of claim 14, wherein the device includes at least one indicator coupled to an inner surface of the first chamber or the second chamber, and the indicator signals when the composition reaches a pH of about 8.4 to about 8.6.

18. The method of claim 14, wherein the composition is applied to the eye within 30 seconds to 2 minutes of combining the acylating agent with the activator liquid.

* * * * *